United States Patent [19]

Honda et al.

[11] Patent Number: 4,495,362

[45] Date of Patent: Jan. 22, 1985

[54] PROCESS FOR PREPARING ALKYL NITROACETATES

[75] Inventors: Tadatoshi Honda, Fujisawa; Yoichi Hosono, Yokohama, both of Japan

[73] Assignee: Mitsui Toatsu Chemicals, Incorporated, Tokyo, Japan

[21] Appl. No.: 439,188

[22] Filed: Nov. 4, 1982

[51] Int. Cl.$^3$ .................... C07C 79/41; C07C 79/42; C07C 79/46

[52] U.S. Cl. ........................ 560/20; 560/21; 560/22; 560/156; 260/404

[58] Field of Search ................ 560/156, 22, 20, 21; 260/404

[56] References Cited

FOREIGN PATENT DOCUMENTS 56-120643  9/1981  Japan ........................ 560/156
56-145245 11/1981  Japan .

OTHER PUBLICATIONS

Allinger, "Organic Chemistry," p. 25, (1971).

*Primary Examiner*—Michael L. Shippen
*Attorney, Agent, or Firm*—Fisher, Christen & Sabol

[57] ABSTRACT

A process for preparing alkyl nitroacetates by reacting an alkyl phenyl carbonate with a nitroparaffin in a polar aprotic solvent in the presence of a cyanide ion. The process permits a higher reaction rate, and thus the reaction can be completed even at room temperature.

12 Claims, No Drawings

PROCESS FOR PREPARING ALKYL NITROACETATES

BACKGROUND OF THE INVENTION

1. Field of the Invention

The present invention relates to a process for preparing alkyl nitroacetates. More particularly, it relates to a process for preparing alkyl nitroacetates by reacting a nitroparaffin with an alkyl phenyl carbonate in the liquid phase.

2. Description of the Prior Art

Alkyl nitroacetates are useful compounds for preparing alpha-nitrocarboxylic acids by reacting the same with alkyl halide, aldehyde, tertiary amines, and the like. It is also well known that production of amino acids such as phenyl alanine, dopa, methyl dopa, tryptophan, alpha-methyltryptophan, etc. is easily carried out by hydrogenating alpha-nitrocarboxylic acids.

There are known various processes for preparing alkyl nitroacetates. For example, (1) Kornblum et al reported in J. Amr. Chem. Soc., 77, 6654 (1955) that ethyl nitroacetates were obtained by reacting ethyl iodoacetate with silver nitrite; (2) Kinkseiner and his coworkers reported in J. Org. Chem., 28, 215 (1963) that a magnesium complex of nitroacetic acid was obtained by reacting nitromethane with methyl carbonate magnesium, which was then subjected to esterification to obtain a nitroacetic acid ester using a strong acid; (3) Zen et al reported in J. Chem. Soc. of Japan, Ind. Chem. Sec., 74, 70 (1971) that methazonic acid salt was obtained by reacting 2 moles of nitromethane with 8 moles of potassium hydroxide, which was then esterified to obtain a nitroacetic acid ester using a strong acid; and (4) Sifniades and others disclosed in J. Org. Chem., 40, 3562 (1975) that a nitroacetoacetic acid ester was obtained by reacting an acetozcetic acid ester with an acyl nitrate, which was then decomposed with an alcohol to obtain a nitroacetic acid ester.

Among the processes mentioned above, the process (2) is not practical as it involves the use of expensive silver salt and metal of magnesium as the starting materials. It is also difficult to put the process (3) to a large scale application as the reaction requires heating of alkali metal salts of nitromethane which entails the dangerous detonation. The process (4), further, necessitates the use of relatively expensive materials such as acetoacetic acid ester and acyl nitrates.

SUMMARY OF THE INVENTION

An object of the present invention is to provide a process for preparing alkyl nitroacetates from a nitroparaffin and an alkyl phenyl carbonate at a higher reaction rate.

Another object of the present invention is to provide a process for preparing alkyl nitroacetate in which the reaction of a nitroparaffin with an alkyl phenyl carbonate can be completed even at room temperature.

In the preparation of alkyl nitroacetates by reacting a nitroparaffin, which is easily obtained in the industry, with an alkyl phenyl carbonate, which is easily produced from phosgen, phenols and alcohols at high yields, the present invention is characterized in that a nitroparaffin is reacted with an alkyl phenyl carbonate in a polar aprotic solvent in the presence of a cyanide ion.

DETAILED DESCRIPTION OF THE INVENTION

Nitroparaffins used as the starting material in the present invention include compounds represented by the formula (I):

wherein $R_1$ and $R_2$ are hydrogen atom, an unsubstituted or substituted alkyl group having 1 to 7 carbon atoms, or an unsubstituted or substituted phenyl group. They are, for example, nitromethane, nitroethane, 1-nitropropane, 2-nitropropane, 1-nitrobutane, 2-nitrobutane, 1-nitroisobutane, 1-nitrooctane, 2-phenylnitroethane, p-chlorophenyl nitromethane, p-nitrophenyl nitromethane, and the like.

Alkyl phenyl carbonates used in the present invention process include compounds represented by the formula (II):

$$ArOCOOR_3 \quad (II)$$

wherein Ar is an unsubstituted or substituted phenyl group, and $R_3$ is an unsubstituted or substituted alkyl group having 1 to 4 carbon atoms. For example, ethyl phenyl carbonate, methyl phenyl carbonate, ethyl p-chlorophenyl carbonate, propyphenyl carbonate, isopropyl phenyl carbonate, butyl phenyl carbonate, methylchloroglycyl carbonate, etc. may be used.

The molar ratio of alkyl phenyl carbonates to nitroparaffins to be used in the present process as the starting materials is in the range of 0.01-100, and more preferably between 0.1-10. When it is outside said range, unreacted materials remain in excess, making the process unpractical.

Cyanide ions present in the reaction system of the present invention process may be added to the same in any arbitrary form. Normally it is added in the form of a salt for easy handling. Cations which form a salt with cyanide ions may be either inorganic or organic cations. The inorganic cations include metal ions of IA, IB, IIA, IIB, VIII groups in the periodic table and ammonium ion, etc. The organic cations include primary, the secondary and the tertiary amines, quarternary ammonium ion and the like. Cyanide ions may also be added to the reaction system in the form of an anion exchange resin adsorbing cyanide ion. This is preferred as an embodiment of the present invention.

There is no specific limit to the amount of cyanide ion added. As the reaction proceeds by the formula (1) below, the reaction rate may be accelerated by using cyanide ions in an amount greater than the equivalent of ArOH formed in the reaction expressed by the formula (1).

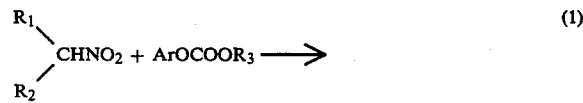

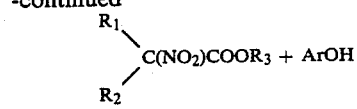

The present invention reaction takes place in a polar aprotic solvent. Acetonitrile, tetrahydrofuran, dioxane, dimethylformamide, dimethylacetamide, dimethyl sufoxide, hexamethylphosphoric triamide, sulfolane, N-methylpyrrolidone, etc. may be used as the solvent.

There is no specific limit to the amount of the solvent. The amount is suitably selected depending on the starting materials, the reaction conditions, and the type of solvents used. The solvent in an amount ten times more than the starting materials or less will normally be sufficient.

There is also no specific limit to the order or the manner of charging the starting materials, cyanide ions and the solvent. If the reaction is in liquid phase, the reaction pressure may be reduced, ambient, or elevated.

The reaction temperature is in the range of from $-20°$ C. to $150°$ C., and more preferably between $0°$ C. and $100°$ C. Although the reaction time varies greatly depending on the temperature, the type of solvent, etc., it is usually in the range of 10 minutes to 20 hours.

The desired product can be obtained by any conventional process such as separating, drying and distilling the reaction solution at a reduced pressure while maintaining pH below 4. In case anion exchange resin of cyanide ion type is employed, the desired product is obtained by filtering the reaction mixture as the product is adsorbed on the resin, and by eluating by using an aqueous solution of a caustic alkali or alkali carbonate, and by separating, drying and distilling at a reduced pressure while maintaining pH of the elute below 4.

The present invention is now described by way of examples.

EXAMPLE 1

6.1 parts of nitromethane (by weight. Hereunder the parts are expressed in the same manner.), 15.2 parts of ethyl phenyl carbonate and 6.5 parts of potassium cyanide are added to 100 parts of dimethyl sulfoxide and the resultant mixture is reacted for 5 hours at room temperature while being agitated. The reaction mixture was added to 150 parts of 1N aqueous solution of acetic acid before adding 100 parts of ethyl acetate for liquid-liquid separation. The ethyl acetate layer thus obtained was washed with water and dried with magnesium sulfate before distilling under reduced pressure to obtain 11.3 parts of the fraction at $68°$ C.–$70°$ C. (2 mmHg). An infrared spectrum of the fraction was identical with that of labelled ethyl nitroacetate. The yield was 85% (based on the starting ethyl phenyl carbonate. Hereunder the yield is expressed in the same manner).

REFERENCE EXAMPLE 1

To 60 parts of dimethyl sulfoxide solution containing 6.1 parts of nitromethane and 15.2 parts of ethyl phenyl carbonate was added 60 parts of dimethyl sulfoxide solution containing 13.2 parts of potassium phenolate, and the resultant mixture was reacted for 5 hours at room temperature while being agitated.

The reaction mixture was then added to 150 parts of 1N aqueous solution of acetic acid before adding 100 parts ethyl acetate for liquid-liquid separation. The ethyl acetate layer thus obtained was washed with water and dried with magnesium sulfate before analysis using high speed liquid chromatography. The product was found to contain 13.9 parts of ethyl phenyl carbonate and 1.0 part of ethyl nitroacetate, The yield was 7.5%.

EXAMPLES 2 TO 6

Experiments were conducted in the same manner as in Reference Example 1 using different types of nitroparaffin, alkyl phenyl carbonate, cyanide and solvent to obtain the results shown in Table 1.

TABLE 1

| Example | Nitroparaffin | Alkyl phenyl carbonate | Cyanide | Solvent | Yield (%) |
|---|---|---|---|---|---|
| 2 | $CH_3NO_2$ | $C_6H_5OCOOCH_3$ | KCN | acetonitrile | 93 |
| 3 | $n-C_4H_9NO_2$ | " | " | " | 73 |
| 4 | $C_6H_5CH_2CH_2NO_2$ | " | " | " | 85 |
| 5 | $CH_3NO_2$ | $C_6H_5OCOOC_2H_5$ | $Et_4NCN$ | " | 95 |
| 6 | " | " | " | DMF | 94 |

Note:
nitroparaffin:alkyl phenyl carbonate:cyanide = 1:1:1 (in mole ratio)

EXAMPLE 7

6.1 parts of nitromethane, 15.2 parts of ethyl phenyl carbonate, and a strong basic anion exchange resin adsorbing 0.1 equivalent part of cyanide ion were added to 100 parts of acetonitrile and left standing for 5 hours at room temperature. The resin was then recovered by filtration, packed in a column and passed with 200 parts of aqueous solution containing 20.0 parts of sodium carbonate. The elute was added with 400 parts of 1N acetic acid and subjected to the identical procedure as in the Reference Example 1. It was found that ethyl nitroacetate was yielded by 90%.

It will be apparent to one of ordinary skill in the art that many changes and modifications can be made to the invention described above without departing from the invention as set forth herein.

What we claim is:

1. A process for preparing an alkyl nitroacetate represented by the formula:

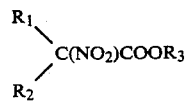

wherein $R_1$ and $R_2$ are a hydrogen atom, a linear or branched alkyl group having 1 to 7 carbon atoms, a benzyl group, a chlorophenyl group, a nitrophenyl group or phenyl group, and $R_3$ is a linear or branched alkyl group having 1 to 4 carbon atoms, comprising reacting a nitroparaffin represented by the formula:

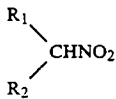

wherein $R_1$ and $R_2$ are the same as described above, with alkyl phenyl carbonate represented by the formula:

ArOCOOR₃ wherein Ar is a chlorophenyl group or a phenyl group and $R_3$ is the same as described above, in a polar aprotic solvent in the presence of cyanide ion.

2. The process as claimed in claim 1 wherein said nitroparaffin is selected from nitromethane, nitroethane, 1-nitropropane, 2-nitropropane, 1-nitrobutane, 2-nitrobutane, 1-nitroisobutane, 1-nitrooctane, 2-phenyl nitroethane, p-chlorophenyl nitromethane or p-nitrophenyl nitromethane.

3. The process as claimed in claim 1 wherein said alkyl phenyl carbonate is selected from ethyl phenyl carbonate, methyl phenyl carbonate, ethyl p-chlorophenyl carbonate ester, propyl phenyl carbonate, isopropyl phenyl carbonate, butyl phenyl carbonate or methyl chloroglycil carbonate.

4. The process as claimed in claim 1 wherein the molar ratio of said nitroparaffin to said alkyl phenyl carbonate is in the range of 1:0.01 to 1:100.

5. The process as claimed in claim 4 wherein the molar ratio of said nitroparaffin to said alkyl phenyl carbonate is in the range of 1:0.1 to 1:10.

6. The process as claimed in claim 1 wherein said cyanide ion is generated from at least a compound selected from the group consisting of cyanides of metals of the IA, IB, IIA, IIB and VIII groups of the periodic table or from ammonium cyanide.

7. The process as claimed in claim 1 wherein said cyanide ion is generated from at least a compound selected from the group consisting of hydrocyanides of primary amines, secondary amines tertiary amines and quaternary ammonium cyanides.

8. The process as claimed in claim 1 wherein the cyanide ion is adsorbed on anion exchange resin.

9. The process as claimed in claim 1 wherein said polar aprotic solvent is selected from acetonitrile, tetrahydrofuran, dioxane, dimethylformamide, dimethylacetamide, dimethyl sulfoxide, hexamethylphsophoric triamide, sulforan or N-methylpyrrolidone.

10. The process as claimed in claim 1 wherein the reaction is conducted at a temperature within the range of −20° to 150° C.

11. The process as claimed in claim 10 wherein the reaction is conducted at a temperature within the range of 0° C. to 100° C.

12. The process as claimed in claim 1, wherein said cyanide ion is adsorbed on an anion exchange resin and the resulting reaction mixture adsorbed on the anion exchange resin is eluted with an aqueous solution of a caustic alkali or alkali carbonate.

* * * * *